US011628108B2

(12) United States Patent
Moore

(10) Patent No.: US 11,628,108 B2
(45) Date of Patent: Apr. 18, 2023

(54) WHEELCHAIR SYSTEMS AND METHODS HAVING A BRACE ASSEMBLY

(71) Applicant: Toyota Motor North America, Inc., Plano, TX (US)

(72) Inventor: Douglas A. Moore, Fairview, TX (US)

(73) Assignee: Toyota Motor North America, Inc., Plano, TX (US)

( * ) Notice: Subject to any disclaimer, the term of this patent is extended or adjusted under 35 U.S.C. 154(b) by 402 days.

(21) Appl. No.: 16/910,583

(22) Filed: Jun. 24, 2020

(65) Prior Publication Data
US 2021/0401643 A1 Dec. 30, 2021

(51) Int. Cl.
*A61G 5/14* (2006.01)
*A61F 5/01* (2006.01)
*A61G 5/04* (2013.01)
*A61G 5/12* (2006.01)

(52) U.S. Cl.
CPC ............... *A61G 5/14* (2013.01); *A61F 5/012* (2013.01); *A61F 5/0116* (2013.01); *A61G 5/04* (2013.01); *A61G 5/12* (2013.01); *A61G 5/127* (2016.11)

(58) Field of Classification Search
CPC .......... A61G 5/14; A61G 5/128; A61G 5/127; A61G 7/1096; A61G 7/1021
USPC ............................ 297/344.15, 344.16, 344.17
See application file for complete search history.

(56) References Cited

U.S. PATENT DOCUMENTS

| 7,967,738 | B2 | 6/2011 | Dauterive |
| 10,245,207 | B2 | 4/2019 | Avni |
| 2009/0218784 | A1* | 9/2009 | Porcheron ............ A61G 5/1075 280/250.1 |
| 2010/0117427 | A1 | 5/2010 | Fukuyama et al. |
| 2015/0060162 | A1* | 3/2015 | Goffer ..................... B60L 15/20 180/41 |
| 2019/0275974 | A1* | 9/2019 | Yetukuri ............... B60R 21/231 |

FOREIGN PATENT DOCUMENTS

| CN | 204814506 U | 12/2015 |
| JP | 2013000469 A | 1/2013 |
| JP | 5876541 B2 | 3/2016 |
| KR | 101915898 B1 | 11/2018 |

OTHER PUBLICATIONS

WO-2021068010-A2, Claassen D G, Apr. 2021. (Year: 2021).*

* cited by examiner

Primary Examiner — Sarah B Mcpartlin
(74) Attorney, Agent, or Firm — Dinsmore & Shohl LLP

(57) ABSTRACT

Systems and methods of wheelchair systems herein provide a wheelchair capable of providing a brace system that moves between retracted and deployed positions to provide a physical support to the legs of the user to assist the user in transition between a plurality of user positions. Embodiments determine a user request for such assistance and then either deploys and/or retracts the brace system. Embodiments provide for assistance independent of additional people, such as aides, to assist the user in moving or transitioning between the plurality of user positions while also allowing or permitting the wheelchair to function normally when the brace system is in the retracted position.

19 Claims, 7 Drawing Sheets

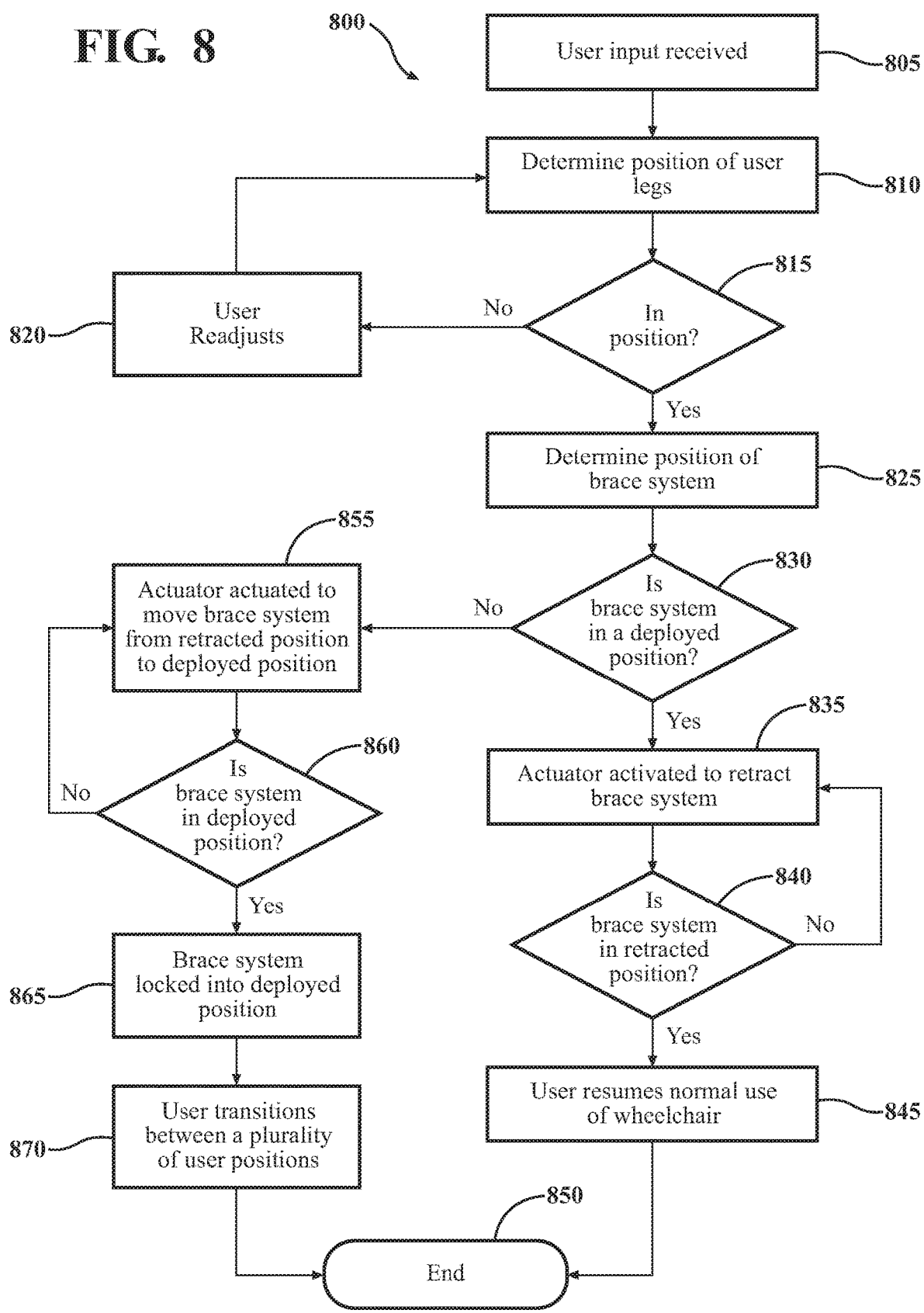

WHEELCHAIR SYSTEMS AND METHODS HAVING A BRACE ASSEMBLY

TECHNICAL FIELD

The present disclosure generally relates to wheelchairs and, more specifically, to wheelchair systems to assist a user to transition between a plurality of user positions.

BACKGROUND

Wheelchairs, such as power wheelchairs, enable those who are unable to walk on their own travel from one place to another. One type of wheelchair is a power wheelchair having one or more motors that allow a user to control the power wheelchair so that it moves under motorized control. Power wheelchairs are useful for people who are unable to use their arms to propel the wheelchair.

In some cases, a user may desire to transition between a plurality of user positions. One example of such a situation is when the user wishes to transition between a seated position and a standing position to reach an object. However, the user may not have assistance in transitioning without the help of an aide, usually a second person. As such, it is difficult for the user to transition into the desired position without assistance by the second person.

Accordingly, a need exists for alternative power wheelchairs that enable assistance in transitioning between a plurality of user positions without assistance from a second person.

SUMMARY

In one embodiment, a wheelchair system is provided. The wheelchair system includes a wheelchair. The wheelchair includes a frame and a brace system coupled to the frame. The brace system includes a pair of braces and one or more inflatable devices coupled to each one of the pair of braces. The one or more inflatable devices are configured to inflate to at least partially circumferentially wrap around a portion of a pair of legs of a user to secure the user to the wheelchair. The brace system is movable between a retracted position and a deployed position such that in the deployed position, the pair of braces stabilize the user of the wheelchair to assist the user to transition between a plurality of user positions.

In another embodiment, a wheelchair system is provided. The wheelchair system includes a wheelchair. The wheelchair includes a frame and a brace system coupled to the frame, a processing device, and a non-transitory, processor-readable storage medium in communication with the processing device. The brace system includes a pair of braces and one or more inflatable devices coupled to each one of the pair of braces. The non-transitory, processor-readable storage medium includes one or more programming instructions that, when executed, cause the processing device to determine when a user request is initiated, and actuate at least one actuator to inflate the pair of braces to move the brace system between a retracted position and a deployed position such that in the deployed position, the pair of braces stabilize the user of the wheelchair to assist the user to transition between a plurality of user positions.

In yet another embodiment, a method of transitioning between a plurality of user positions is provided. The method includes determining when a user request is initiated, and actuating at least one actuator to inflate a pair of braces to move a brace system between a retracted position and a deployed position such that in the deployed position, the pair of braces stabilize a user of a wheelchair to assist the user to transition between a plurality of user positions and in the retracted position, each one of the pair of braces are housed in a receiving cavity so to be out of the way for a normal use of the wheelchair.

These and additional objects and advantages provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 8 graphically depicts a flowchart of an example method of a wheelchair system for moving a brace system between a retracted position and a deployed position to assist a user to transition between a plurality of user positions.

DETAILED DESCRIPTION

The systems and methods described herein generally relate to a powered wheelchair configured with a brace system that is movable between a retracted position and a deployed position. The retracted position permits a normal use of the powered wheelchair. The deployed position extends around an upper portion of the user legs and/or a lower portion of the user's legs to provide support and rigidity to assist the user in transitioning between a plurality of user positions. Present power wheelchairs do not have brace systems that may be an add-on feature to assist the user in transitioning between the plurality of user positions independent of aid from a second person. As a non-limiting example, the user may wish to stand to reach an object that could not be otherwise reached with the user seated in the power wheelchair. Without an aide, the user may not be able to stand, lose their balance and fall, take several attempts to stand, and the like. After using the leg brace system, the user may actuate the system to move the leg brace system into the retracted position such that normal functionality of the powered wheelchair may resume.

Various embodiments of power wheelchairs configured with brace systems that are movable between a retracted position and a deployed to assist a user in transitioning between a plurality of user positions are described in detail herein.

As used herein, the term "communicatively coupled" may mean that coupled components are capable of exchanging data signals with one another such as, for example, electrical signals via conductive medium or a non-conductive medium, though networks such as via Wi-Fi, Bluetooth, and the like, electromagnetic signals via air, optical signals via optical waveguides, and the like.

Figure 1:
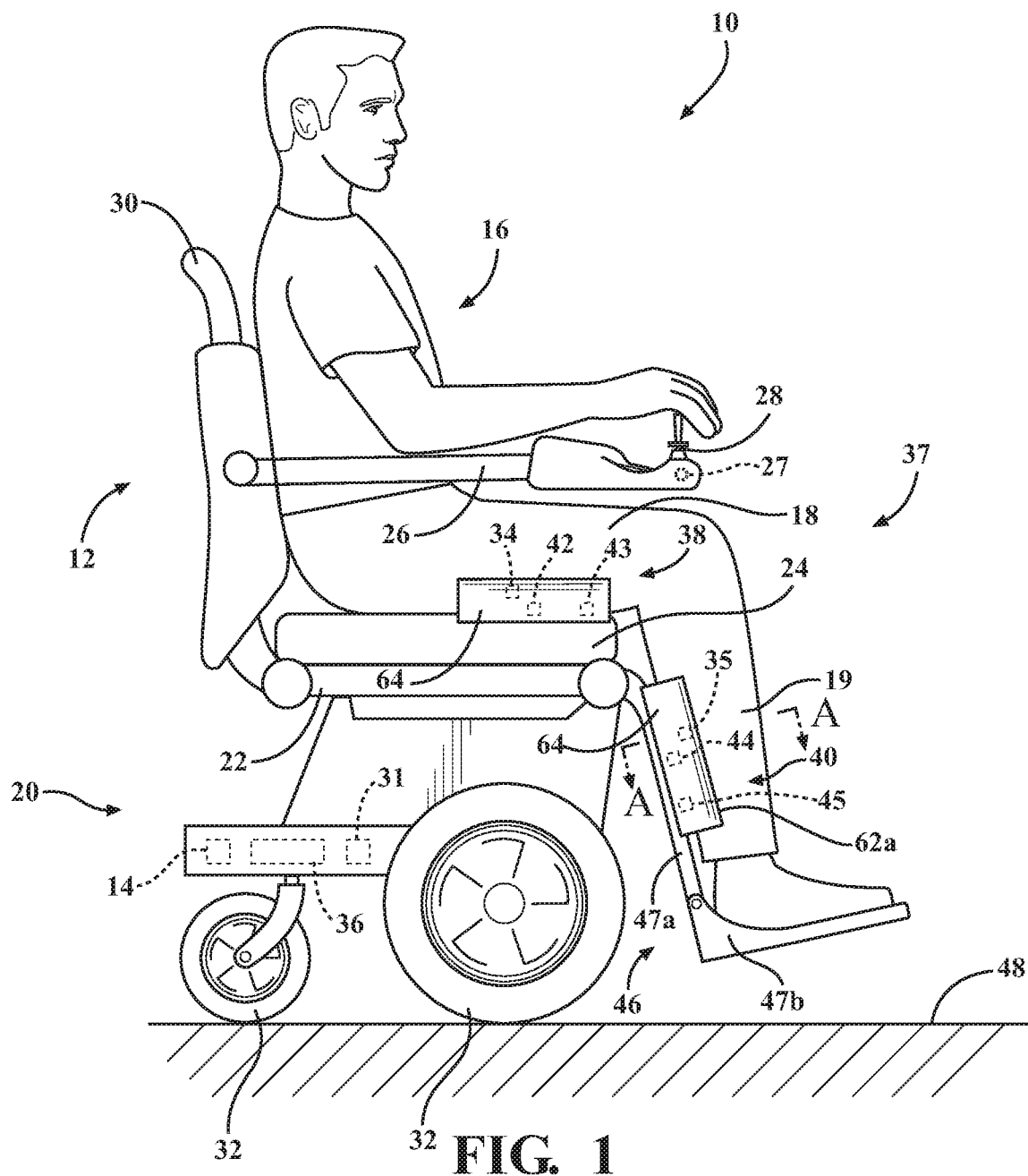
FIG. 1 schematically depicts an example wheelchair system having a brace system according to one or more embodiments described and illustrated herein.

As used herein, the term "system longitudinal direction" refers to the forward-rearward direction of the system (i.e., in a +/−X direction of the coordinate axes depicted in FIG. 1). The term "system lateral direction" refers to the cross-direction (i.e., along the Y axis of the coordinate axes depicted in FIG. 1), and is transverse to the longitudinal direction. The term "system vertical direction" refers to the upward-downward direction of the system (i.e., in the +/−Z direction of the coordinate axes depicted in FIG. 1). As used herein, "upper" or "uppermost" is defined as generally being towards the positive Z direction of the coordinate axes shown in the drawings. "Lower" or "lowermost" is defined as generally being towards the negative Z direction of the coordinate axes shown in the drawings.

Figure 2:
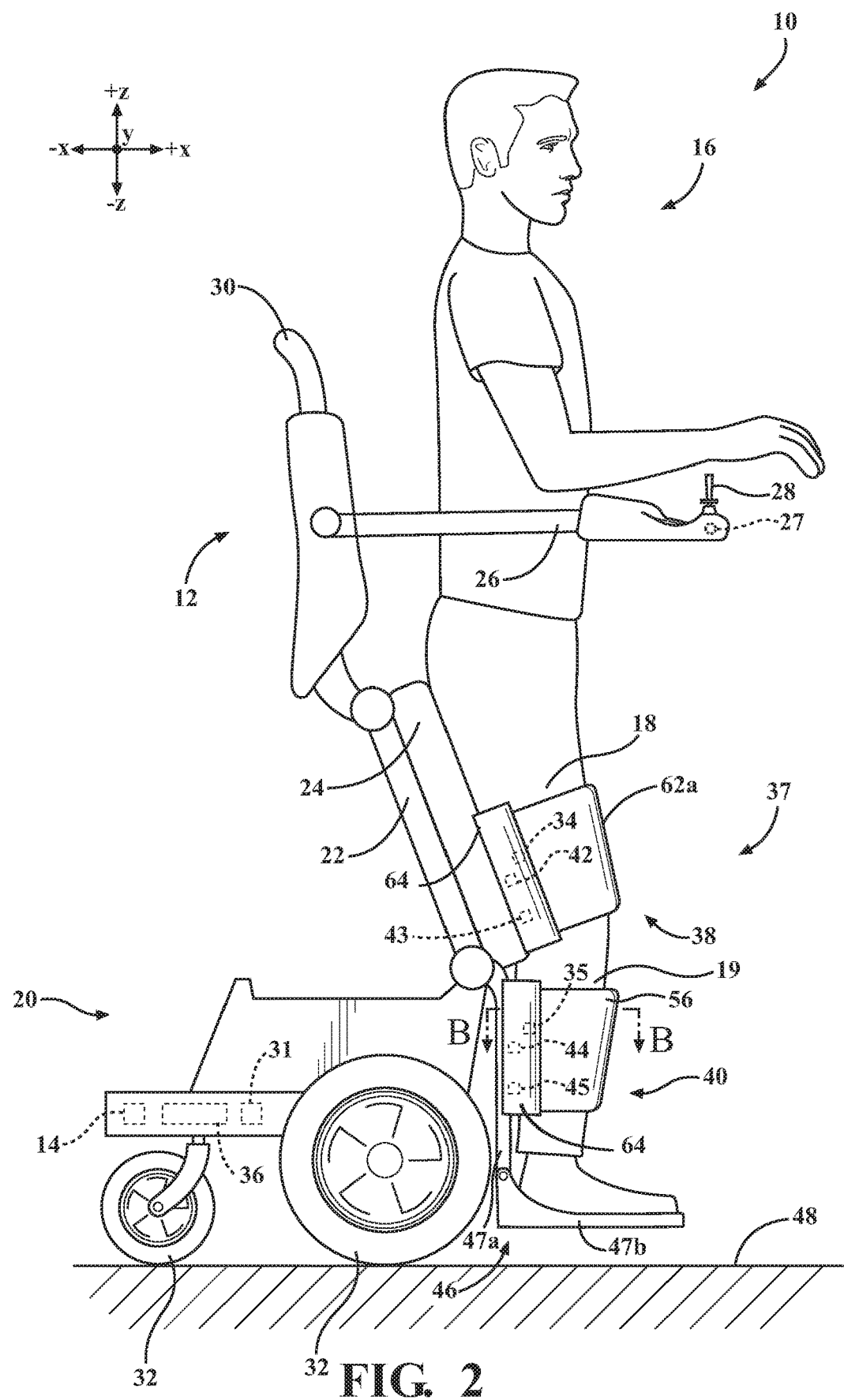
FIG. 2 schematically depicts the example wheelchair system of FIG. 1 wherein the brace system is in a deployed position and a user is standing according to one or more embodiments described and illustrated herein.

Referring initially to FIGS. 1-2, a schematic depiction of an example wheelchair system, generally designated 10, is provided. The system 10 generally includes a wheelchair 12. The wheelchair includes a control unit 14. In some embodiments, the wheelchair 12 is a powered wheelchair that includes motorized components that allow a user 16 to electronically control movement of the wheelchair. Accordingly, various components of the wheelchair 12 should be understood and are not described in further detail herein. In other embodiments, the wheelchair 12 may be human powered or manually advanced in travel. In some embodiments, the wheelchair 12 may include a power base portion 20, a frame 22, and a seat portion 24 supported by the frame 22, which in turn is supported by the power base portion 20. Thus, the frame 22 is generally positioned below the seat portion 24 in a system vertical direction (i.e., positioned in the −Z direction of the coordinate axes of FIG. 1 relative to the seat portion 24) and the power base portion 20 is generally positioned below the frame 22 in a system vertical direction (i.e., positioned in the −Z direction of the coordinate axes of FIG. 1 relative to the frame 22).

The frame 22 may further include a footrest assembly 46 that includes an elongated member portion 47a that is hingedly and/or pivotally coupled to a foot support portion 47b. The elongated member may be pivotally coupled to the frame 22 adjacent to seat portion 24 such that the elongated member portion 47a moves between a sitting position, as best seen in FIG. 1, and a standing position, as best seen in FIG. 2. It should be appreciated that the length of the elongated member portion 47a may adjust mechanically by a tension member, such as a spring, and/or electrically, to accommodate for a plurality of heights and/or a plurality of weights of users. Further, it should be appreciated that the length, width, angle, tilt, and the like of the foot support portion 47b may adjust mechanically by a tension member, such as a spring, and/or electrically, to accommodate for a plurality of sizes and/or a plurality of weights of users. Further, it should be appreciated that the footrest assembly 46 may not be used to support feet of the user and instead the feet of the user are in contact with a surface 48, such as a floor, such that the user may stand to reach the object, as discussed in greater detail herein.

Still referring to FIGS. 1-2, in some embodiments, the power base portion 20 may raise, tilt, or otherwise move the frame 22 and thus the seat portion 24. The frame 22 and the seat portion 24 are generally configured to support the user 16 when the user 16 is seated in the wheelchair 12. In some embodiments, the seat portion 24 may include a pair of armrests 26 to which a controller 28 may be coupled. As described herein, a controller 28 may provide the user 16 with an ability to control movement of the wheelchair 12. In some embodiments, the controller 28 may be a joystick-type controller where the user 16 directs the joystick in accordance with a desired direction and/or speed of travel. Accordingly, the controller 28 may be communicatively coupled to the power base portion 20, including various components thereof, to transmit signals to the power base portion 20 to cause the wheelchair 12 to respond according to the inputs received by the controller 28. It should be understood that the joystick configuration is merely illustrative, and in some embodiments, the controller 28 may utilize other designs, such as buttons, switches, voice controls, breath controls, and/or the like to receive inputs from a user 16 via a user interface and the like.

In some embodiments, the seat portion 24 may include one or more handles 30 integrated therein or coupled thereto. The one or more handles 30 may provide an area for a user (e.g., a caregiver) to grip the wheelchair 12. For example, at least one of the one or more handles 30 may be located on a back portion of the seat portion 24 such that a user may grasp the one or more handles 30 when moving behind the wheelchair 12.

A brace system 37 may be coupled to the frame 22. In some embodiments, the brace system 37 is integrally formed with the frame 22. In other embodiments, the brace system 37 is an add-on feature (e.g., aftermarket purchase and then installed to be coupled to the frame 22). The brace system 37 may include at least one brace assembly 38. It should be appreciated that, as illustrated, the brace system 37 includes a second brace assembly 40. The at least one brace assembly 38 may positioned at an upper leg portion 18 of the user 16 and the second brace assembly 40 may be positioned at a lower leg portion 19 of the user 16.

Still referring to FIGS. 1-2, the at least one brace assembly 38 further includes a first actuator 34 and a first position sensor 42. The first position sensor 42 is communicatively coupled to the control unit 14 and is configured to determine a position of the at least one brace assembly 38 (e.g. whether in a deployed position and/or a retracted position), to determine a position of the upper leg portion 18 of the user 16, and the like. The first actuator 34 is communicatively coupled to the control unit 14 and is fluidly coupled to the at least one brace assembly 38 to actuate or move the at least one brace assembly 38 between the deployed position and the retracted position, as discussed in greater detail herein.

The second brace assembly 40 further includes a second actuator 35 and a second position sensor 44. The second position sensor 44 is communicatively coupled to the control unit 14 and is configured to determine a position of the second brace assembly 40 (e.g. whether in a deployed position and/or a retracted position), to determine a position of the lower leg portion 19 of the user 16, and the like. The second actuator 35 is communicatively coupled to the control unit 14 and is fluidly coupled to the second brace assembly 40 to actuate or move the second brace assembly 40 between the deployed position and the retracted position, as discussed in greater detail herein.

The power base portion 20 may include, but is not limited to, one or more wheels 32, a drive actuator 31, a battery 36, and the control unit 14. The control unit 14 may be an electronic control unit and may generally be a control device that controls the wheelchair 12 and/or one or more components thereof (e.g., the first actuator 34, the second actuator 35, the first position sensor 42 and/or the second position sensor 44). As such, the control unit 14 may be communicatively coupled to the various components of the wheelchair 12 such that one or more control signals can be transmitted from the control unit 14 to the various components such as the first actuator 34 and the second actuator 35, as described in greater detail herein. The drive actuator 31, which may be configured as one or more motors, is coupled to the wheels 32 to drive movement of the wheels 32. The battery 36 may generally provide electrical power to the various components of the wheelchair 12, such as the drive actuator 31, the first actuator 34, and the second actuator 35. Other components of the power base portion 20 should generally be understood and are not described in further detail herein.

The one or more wheels 32 may be configured as any type of wheel. As a non-limiting example, the one or more wheels 32 may be omni-directional wheels, which may enable a user to easily move the wheelchair 12 in any direction when it is in the fine manual motion control described below.

The control unit 14 may generally be a standalone control device that contains one or more components for controlling movement of the wheelchair 12. It should be appreciated that while the control unit is shown in FIGS. 1-7 as part of the power base portion 20 of the wheelchair 12, this is a non-limiting example. That is, the control unit 14 may be a device that is separate from the power base portion 20, such as a device that is coupled to or integrated with the pair of armrests 26, the seat portion 24, and/or the like. In some embodiments, the control unit 14 may be separate from the wheelchair 12 altogether, such as, for example, a user carried computing device, the user's mobile device, and/or the like.

Now referring to FIGS. 3-4, a first aspect of the example brace system 37 will be discussed. It should be appreciated that the at least one brace assembly 38 and the second brace assembly 40 of the brace system 37 are identical and have identical components. As such, in the following paragraphs, only the second brace assembly 40 will be described in greater detail. Further, it should be understood that the second brace assembly 40 will be referred to as the brace assembly 40, the second actuator 35 as the actuator 35, and the like. It should be understood that there may be a plurality of brace assemblies coupled to the frame 22 of the wheelchair.

The example brace assembly 40 includes a pair of flexible braces 60*a*, 60*b*. The pair of flexible braces 60*a*, 60*b* are fluidly coupled to the actuator 35 by a fluid member 71. The fluid member 71 may be a tube, a hose, conduit, and the like. Further, the fluid member 71 may be a regular or uniform shape or be an irregular shape. A first end 73 of the fluid member 71 is fluidly coupled to the actuator 35 and a second end 75 of the fluid member 71 is fluidly coupled to at least one bladder 54 of each one of the pair of flexible braces 60*a*, 60*b*. The at least one bladder 54 may be a vessel that is configured to hold a fluid, such as air, gas, water, and the like, and to expand and contract based on the amount of fluid that is held in the at least one bladder 54.

Each of the pair of flexible braces 60*a*, 60*b* includes an exterior surface 62*a* and an opposite interior surface 62*b* in which the interior surface 62*b* may make contact with the lower leg portion 19 of the user 16 (FIG. 1) when each one of the pair of flexible braces 60*a*, 60*b* are in the deployed position. In some embodiments, the interior surface 62*b* may be a more rigid material than the exterior surface 62*a*. That is, the exterior surface 62*a* may be more flexible than the interior surface 62*b* such that when each of the pair of flexible braces 60*a*, 60*b* move between the retracted position, as best seen in FIG. 3, and the deployed position, as best seen in FIG. 4, or vice versa, each of the pair of flexible braces 60*a*, 60*b* navigate around the lower leg portion 19 of the user 16. It should be understood that in some embodiments, each of the pair of flexible braces 60*a*, 60*b* at least partially circumferentially wrap around a portion of the lower leg portion 19 of the legs of the user 16 to secure the user 16 to the wheelchair 12 in the deployed position.

Figure 3:
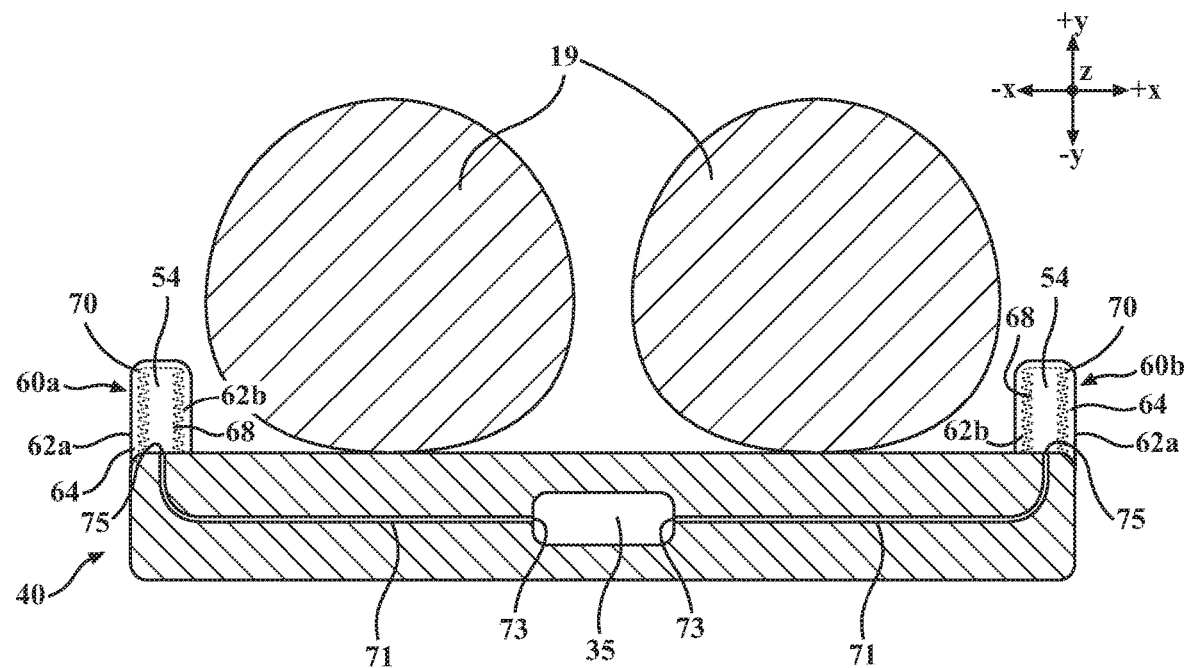
FIG. 3 schematically depicts a partial cross sectional view of a first aspect of the example wheelchair system of FIG. 1 taken from line A-A wherein the brace system is in a retracted position according to one or more embodiments described and illustrated herein.
Figure 4:
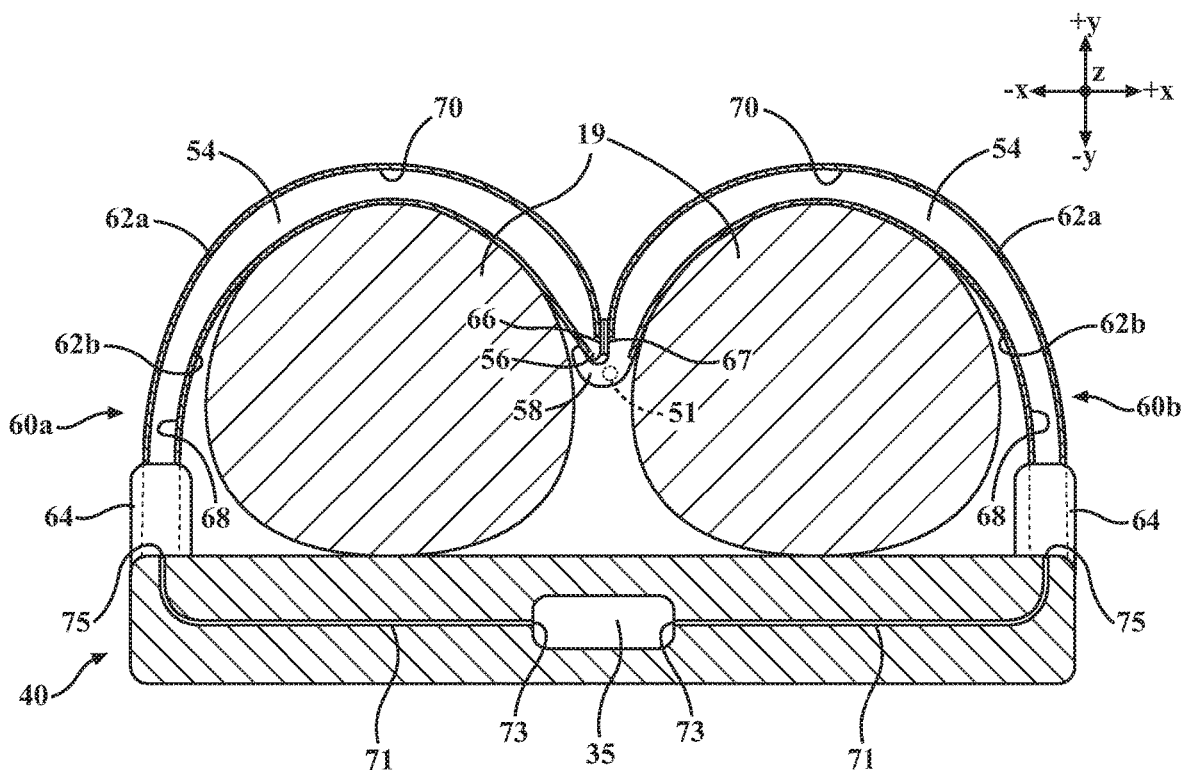
FIG. 4 schematically depicts a partial cross sectional view of a first aspect of the example wheelchair system of FIG. 2 taken from line B-B wherein the brace system is in a deployed position according to one or more embodiments described and illustrated herein.

Still referring to FIGS. 3-4, the at least one bladder 54 of each one of the pair of flexible braces 60*a*, 60*b* may be positioned between the exterior surface 62*a* and the interior surface 62*b*. As such, at least one bladder 54 of each one of the pair of flexible braces 60*a*, 60*b* may push against the exterior surface 62*a* and/or the interior surface 62*b* of each one of the pair of flexible braces 60*a*, 60*b* when inflated by the fluid to move of each one of the pair of flexible braces 60*a*, 60*b* between the retracted position and the deployed position. The at least one bladder 54 of each one of the pair of flexible braces 60*a*, 60*b* includes an inner surface 68 and an opposite outer surface 70. The outer surface 70 of the at least one bladder 54 may be adjacent to, or abut the material that forms the exterior surface 62*a* of each of the pair of flexible braces 60*a*, 60*b*. The inner surface 68 of the at least one bladder 54 may be adjacent to, or abut the material that forms the interior surface 62*b* of each of the pair of flexible braces 60*a*, 60*b*.

The flexible brace 60*a* of the pair of flexible braces 60*a*, 60*b* includes a distal end 56. The flexible brace 60*b* of the pair of flexible braces 60*a*, 60*b* includes a distal end 58. The distal end 56 of the flexible brace 60*a* of the pair of flexible braces 60*a*, 60*b* may taper as it terminates. The distal end 58 of the flexible brace 60*b* of the pair of flexible braces 60*a*, 60*b*, in some embodiments, may be generally a hook shape. That is, the distal end 58 includes a radius that is configured to receive at least a portion of the distal end 56 of the flexible brace 60*a* when the pair of flexible braces 60*a*, 60*b* are in the deployed position. It should be appreciated that the generally hook shape of the distal end 58 is configured to mate, connect and/or join the flexible brace 60*a* to the flexible brace 60*b* in the deployed position. That is, the interior surface 62*b* of the distal end 56 of the flexible brace 60*a* may abut the exterior surface 62*a* of the distal end 58 of the flexible brace 60*b* when the distal end 56 is received in the hook shape of the distal end 58.

In other embodiments, the 58 of the flexible brace 60b may be a "J" shape, an "L" shape, and/or any other shape that may mate, connect, and/or join the flexible brace 60a to the flexible brace 60b in the deployed position. It should be understand that by mating, connecting, and/or joining the flexible brace 60a to the flexible brace 60b in the deployed position, additional structure, strength, and stability may be generated in the brace system 37 (FIG. 1).

Still referring to FIGS. 3-4, in some embodiments, the exterior surface 62a near or adjacent to the distal end 56 of the flexible brace 60a may further include an attachment portion 66. In some embodiments, the attachment portion 66 may be a receiving cavity, a void, a channel, a hook and loop fastener, a catch, and/or the like. Further, in some embodiments, the exterior surface 62a near or adjacent to the distal end 58 of the flexible brace 60b may further include an engagement portion 67. The engagement portion may be a J-hook, a mushroom-hook, a hook and loop fastener, a catch, and/or the like. In the deployed position, the attachment portion 66 of the flexible brace 60a receives at least a portion of the engagement portion 67 of the flexible brace 60b to assist in the mating, connecting, and/or joining of the flexible brace 60a to the flexible brace 60b in the deployed position. It should be understood that the attachment portion 66 of the flexible brace 60a receiving at least a portion of the engagement portion 67 assists in providing additional structure, strength, and stability in the brace system 37 (FIG. 1).

Further, it should be appreciated that for the distal end 58 of the flexible brace 60b may extend in the system longitudinal direction (i.e., in the −X direction) a greater distance than the distal end 56 of the flexible brace 60a before being seated into the deployed position, as discussed in greater detail herein. That is, the distal end 58 of the flexible brace 60b may move with a greater radius with respect to the leg of the user 16 and/or the distal end 56 of the flexible brace 60a such that the distal end 58 of the flexible brace 60b overlaps with the distal end 56 of the flexible brace 60a in the deployed position. It should be appreciated that the seated position may occur when the distal end 58 of the flexible brace 60b is retracted slightly in the system longitudinal direction (i.e., in the +X direction) so to mate or hook the distal end 58 of the flexible brace 60a with the distal end 56 of the flexible brace 60a. Further, it should be appreciated that this movement may also cause the engagement portion 67 of the flexible brace 60b to connect, or engage, with the attachment portion 66 of the flexible brace 60a. It should be understood that his process may be reversed to disconnect, or unjoin, the distal end 58 of the flexible brace 60b from the distal end 56 of the flexible brace 60a and/or the engagement portion 67 of the flexible brace 60b from the attachment portion 66 of the flexible brace 60a.

It should be appreciated that the at least one bladder 54, at least a portion of the exterior surface 62a and/or a portion of the interior surface 62b, such as the distal ends 56, 58 of each one of the pair of flexible braces 60a, 60b, respectively, may be stored or housed within a receiving portion 64 when the pair of flexible braces 60a, 60b are in the retracted position, as best shown in FIG. 3. The receiving portion 64 may be as a cavity, a void, and the like. The receiving portion 64 of the brace assembly 40 may be static with respect to the at least one bladder 54 of each of the pair of flexible braces 60a, 60b. That is, regardless of the position of the pair of flexible braces 60a, 60b, the receiving portion 64 may not move.

Figure 5:
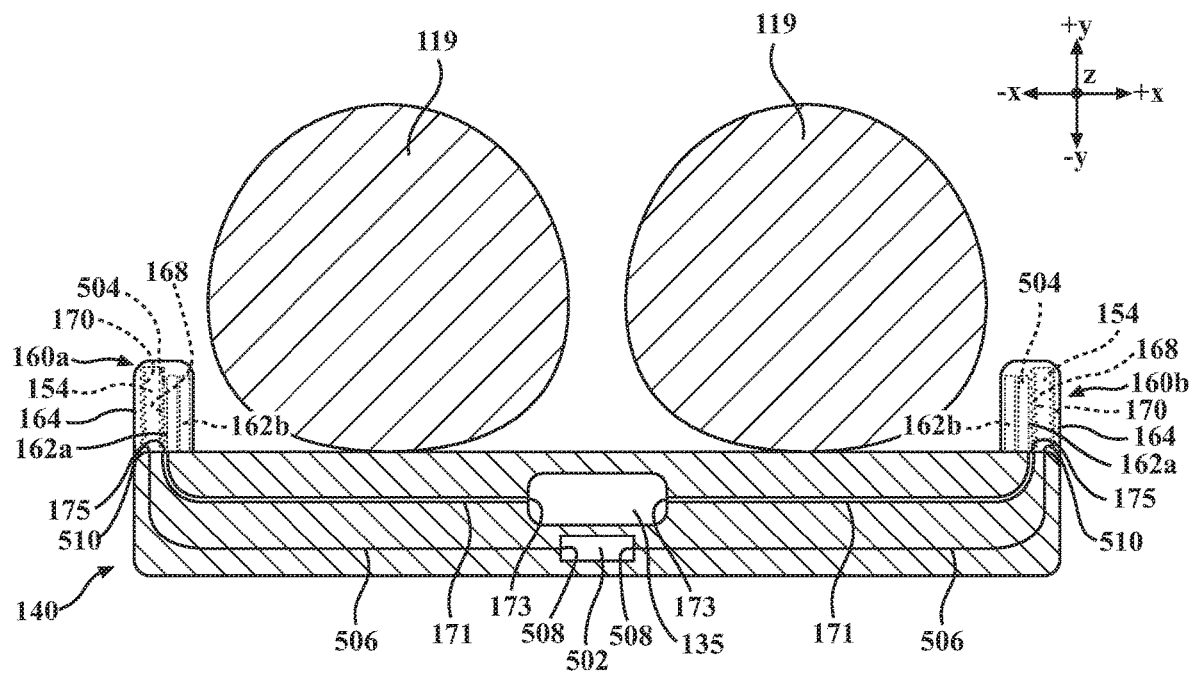
FIG. 5 schematically depicts a partial cross sectional view of a second aspect of the example wheelchair system of FIG. 1 taken from line A-A wherein the brace system is in a retracted position according to one or more embodiments described and illustrated herein.
Figure 6:
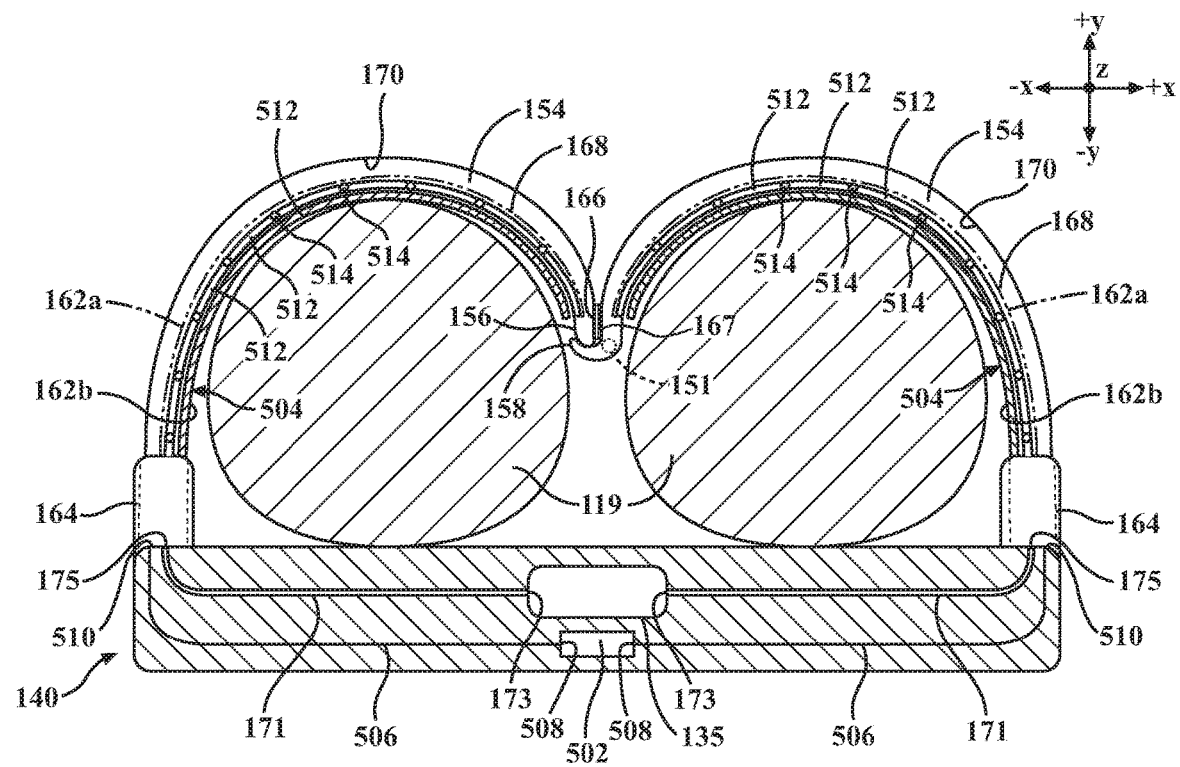
FIG. 6 schematically depicts a partial cross sectional view of a second aspect of the example wheelchair system of FIG. 2 taken from line B-B wherein the brace system is in a deployed position according to one or more embodiments described and illustrated herein.

Referring now to FIGS. 5-6, a second aspect of a brace system 137 is schematically depicted. It is understood that the brace system 137 is similar to the brace system 37 with the exceptions of the features described herein. As such, like features will use the same reference numerals with a prefix "1" for the reference numbers. As such, for brevity reasons, these features will not be described again.

The brace system 137 includes the brace assembly 140, which further includes the pair of flexible braces 160a, 160b. Each of the pair of flexible braces 160a, 160b may include an exterior surface 162a and an opposite interior surface 162b in which the interior surface 162b may make contact with the lower leg portion 119 of the user 116 (FIG. 1) when each one of the pair of flexible braces 160a, 160b are in the deployed position. In some embodiments, the interior surface 162b and the exterior surface 162a may be a similar material having a similar stiffness. It should be appreciated that the interior surface 162b and the exterior surface 162a of the flexible braces 160a, 160b may have a stiffness that is the same and/or less than the stiffness of the exterior surface 62a (FIG. 3) of the of the pair of flexible braces 60a, 60b (FIG. 3), as discussed above. That is, in some embodiments, the interior surface 162b and the exterior surface 162a of the flexible braces 160a, 160b may be more flexible, or pliable than the interior surface 62b (FIG. 3) of the of the pair of flexible braces 60a, 60b (FIG. 3), as discussed above.

Still referring to FIGS. 5-6, the at least one bladder 154 of each one of the pair of flexible braces 160a, 160b may be positioned between the interior surface 162b and the exterior surface 162a. In other embodiments, the at least one bladder 154 is positioned on the exterior surface 162a. As such, at least one bladder 154 of each one of the pair of flexible braces 160a, 160b may push, pull, and/or somehow move the exterior surface 162a and/or the interior surface 162b of each one of the pair of flexible braces 160a, 160b when inflated by the fluid to move each one of the pair of flexible braces 160a, 160b between the retracted position and the deployed position. The at least one bladder 154 of each one of the pair of flexible braces 160a, 160b includes an inner surface 168 and an opposite outer surface 170. In some embodiments, the inner surface 168 of the at least one bladder 154 may be adjacent to, or abut the material that separates components of each of the pair of flexible braces 160a, 160b, as discussed in greater detail below.

The brace assembly 140 further includes a linkage actuator 502. The linkage actuator 502 is communicatively coupled to the control unit 14 and is mechanically coupled to a linkage assembly 504 to actuate or assist in moving each one of the pair of flexible braces 160a, 160b between the deployed position and the retracted position, as discussed in greater detail herein. Further, the linkage assembly 504 may provide a support structure for the user to move or transition between the plurality of user positions, as discussed in greater detail herein.

The linkage actuator 502 may be mechanically coupled to a linkage assembly 504 by an elongated member 506. The elongated member 506 may be a flexible member, a rigid member, a conduit, and the like. Further, the elongated member 506 may be a regular or uniform shape or be an irregular shape. A first end 508 of the elongated member 506 is mechanically coupled to the linkage actuator 502 and a second end 510 of the elongated member 506 is mechanically coupled to the linkage assembly 504 of each one of the pair of flexible braces 160a, 160b. It should be appreciated that mechanically coupled may be by a fastener, such as a bolt and a nut, a rivet, and a screw, or by a clip, a ring, or other device that may couple two elements together.

Still referring to FIGS. 5-6, the linkage assembly 504 of each one of the pair of flexible braces 160a, 160b may be positioned between the exterior surface 162a and the interior surface 162b. As such, the linkage assembly 504 of each one of the pair of flexible braces 160a, 160b assist in may pushing against and/or pulling on the exterior surface 162a and/or the interior surface 162b of each one of the pair of flexible braces 160a, 160b when the linkage assembly 504 is moved into from a retracted position into an extended position via the linkage actuator 502. As such, the linkage assembly 504 in conjunction with the at least one bladder 154 assist in moving each one of the pair of flexible braces 160a, 160b between the retracted position and the deployed position. Further, the linkage assembly 504 and/or the at least one bladder 154 provides additional support to the legs of the user 16 (FIG. 1) to assist the user 16 in transitioning between the plurality of user positions.

In some embodiments, the linkage assembly 504 may be a plurality of independent links 512 coupled to one another by a pivot mechanism 514, such as a hinge pin, a dowel, and the like. As such, each one of plurality of independent links 512 may follow the radius or contour of the exterior and/or interior surfaces 162a, 162b of the pair of flexible braces 160a, 160b. In other embodiments, the linkage assembly 504 may single link that is configured to be rigid enough to provide support and flexible enough to follow the radius and contour of the exterior and/or interior surfaces 162a, 162b of the pair of flexible braces 160a, 160b. Further, the second position sensor 144 is further configured to determine a position of the linkage assembly 504.

It should be appreciated that the at least one bladder 154, the linkage assembly 504, at least a portion of the exterior surface 162a and/or a portion of the interior surface 162b, such as the distal ends 156, 158 of each one of the pair of flexible braces 160a, 160b, respectively, may be stored or housed within a receiving portion 164 when the pair of flexible braces 160a, 160b are in the retracted position, as best shown in FIG. 5. The receiving portion 164 may be as a cavity, a void, and the like. The receiving portion 164 of the brace assembly 140 may be static with respect to the at least one bladder 154 and/or the linkage assembly 504 of each of the pair of flexible braces 160a, 160b. That is, regardless of the position of the pair of flexible braces 160a, 160b, the receiving portion 164 may not move.

Figure 7A:
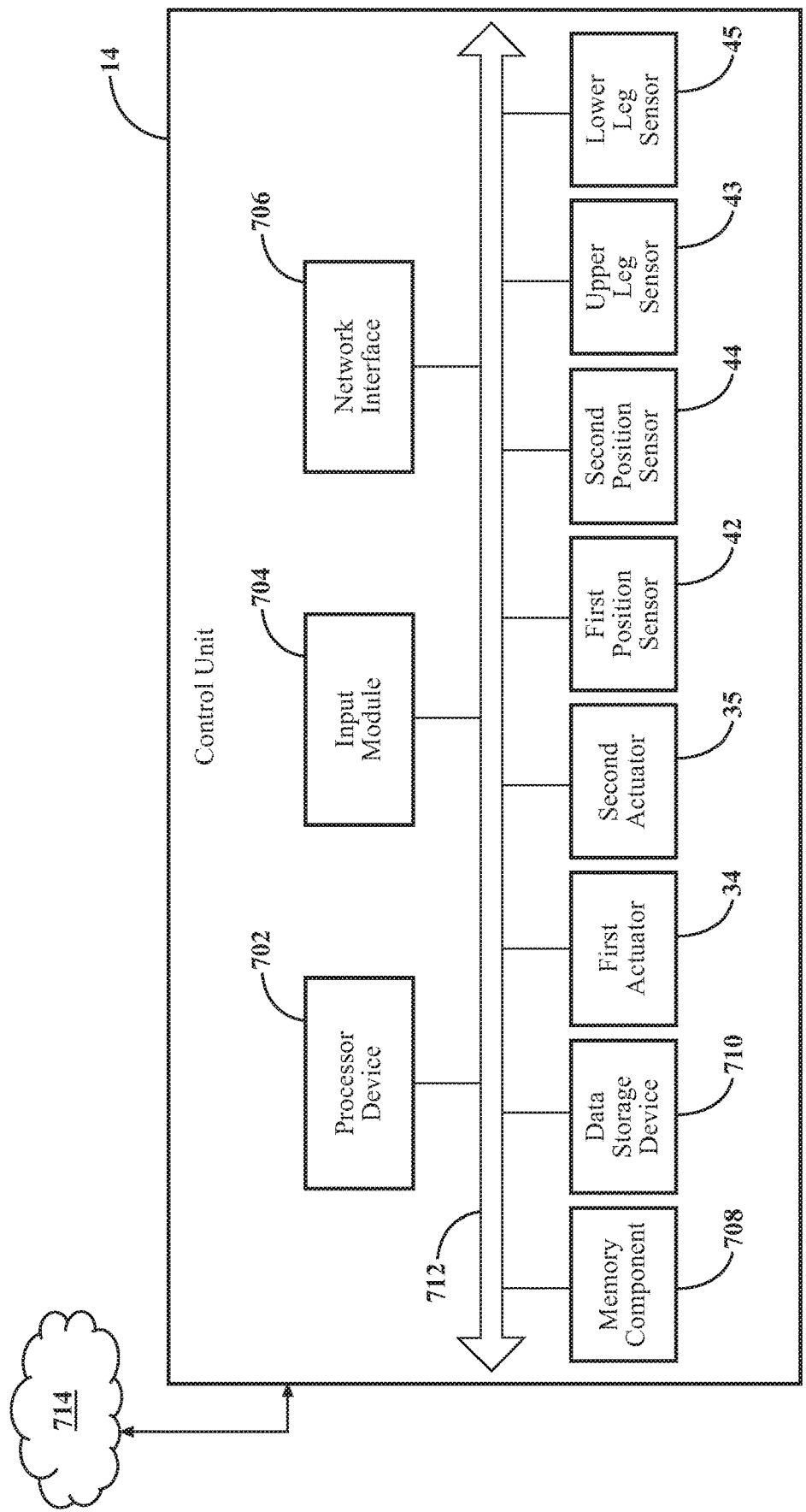
FIG. 7A schematically depicts components of an example control unit of an example wheelchair system according to one or more embodiments described and illustrated herein.

Referring to FIGS. 1 and 7A, various illustrative components of the control unit 14 are schematically depicted. In various embodiments, the control unit 14 includes a network interface 706, a processing device 702, a data storage device 710, and a memory component 708. The processing device 702, such as a computer processing unit (CPU), may be the central processing unit of the control unit 14, performing calculations and logic operations to execute a program. The processing device 702, alone or in conjunction with the other components, is an illustrative processing device, computing device, processor, or combination thereof. The processing device 702 may include any processing component configured to receive and execute instructions (such as from the memory component 708). A local interface 712, such as a bus or other medium configured to transmit and/or receive signals, power, or the like, may interconnect the various components.

In some embodiments, the memory component 708 may be configured as a volatile and/or a nonvolatile computer-readable medium and, as such, may include random access memory (including SRAM, DRAM, and/or other types of random access memory), read only memory (ROM), flash memory, registers, compact discs (CD), digital versatile discs (DVD), and/or other types of storage components. Further, the memory component 708 may be a non-transitory, processor-readable memory. The memory component 708 may include one or more programming instructions thereon that, when executed by the processing device 702, cause the processing device 702 to complete various processes, such as one or more of the processes described herein with respect to FIG. 8.

Figure 7B:
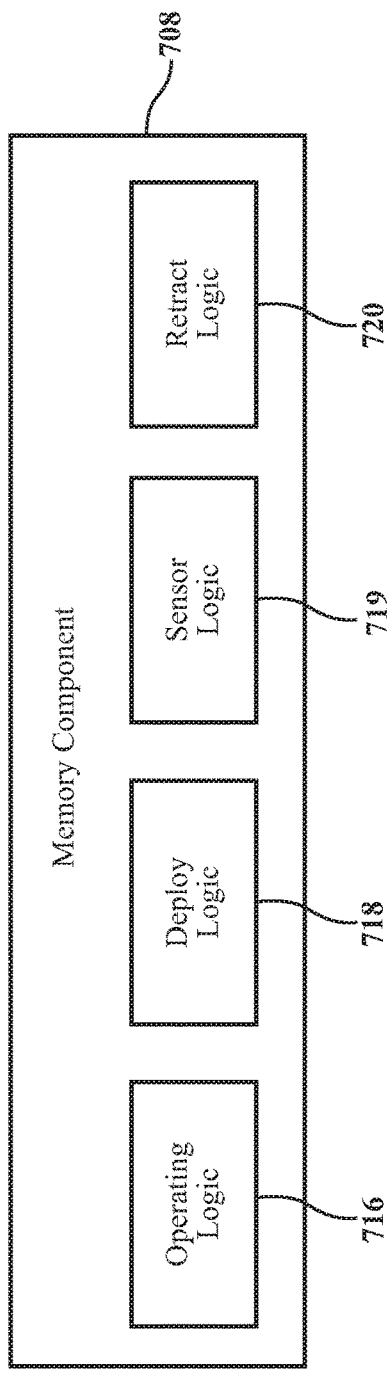
FIG. 7B schematically depicts logic modules of an example memory component of the example wheelchair system of FIG. 7A according to one or more embodiments described and illustrated herein.

Referring to FIG. 7B, the programming instructions stored on the memory component 708 may be embodied as one or more software logic modules, where each logic module provides programming instructions for completing one or more functions, such as the functions described in greater detail below with respect to FIG. 8. For instance, a wheelchair operating logic module 716 may include one or more different pieces of logic, each of which may be embodied as a computer program, firmware, and/or software/hardware, which may be executable by the processing device 702 to cause the wheelchair 12 to move and/or orientate itself with respect to commands provided by the user 16.

A deploy logic module 718 may include one or more pieces of logic, each of which may be embodied as a computer program, firmware, and/or software/hardware, which may be executable by the processing device 702 to determine and inflate the brace system 37 (FIG. 1) into the deployed position to provide additional support to the legs (e.g., upper leg portion 18 (FIG. 1) and/or lower leg portion 19 (FIG. 1)) of the user 16 so that the user 16 may transition between a plurality of user positions (e.g., from a sitting position to a standing position).

A sensor logic module 719 may include one or more pieces of logic, each of which may be embodied as a computer program, firmware, and/or software/hardware, which may be executable by the processing device 702 to receive a process signals and/or data from one or more sensors, such as the sensors illustrated in FIGS. 1-6.

A retract logic module 720 may include one or more pieces of logic, each of which may be embodied as a computer program, firmware, and/or software/hardware, which may be executable by the processing device 702 to determine when and to deflate and store or house the brace system 37 (FIG. 1) into the retracted position such that the user 16 may operate the wheelchair 12 in a typical or normal manner.

Referring once again to FIG. 7A, an input module 704 is provided to enable the user 16 to input controls into the control unit 14 and thus the wheelchair 12. The input module 704 may be communicatively coupled to the controller 28 and/or another input device (e.g., switch 27), as described in more detail below. The input module 704 may communicate input signals to the processing device 702, for example, such that the user 16 may request for the brace system 37 to move between the deployed and retracted positions via the first actuator 34 and/or the second actuator 35. Thus, it should be appreciated that the user controls, as discussed in greater detail herein, may be transmitted to the control unit 14 through the input module 704. Further, it should be appreciated that the user 16 may select the user controls by a button, such as a push button, a switch, such as a toggle switch, and the like on the wheelchair 12 including from on the pair of armrests 26 or from a program selection initiated at an external device such as a portable computing device, smartphone, or the like by way of the network interface described below 706.

The network interface 706 of the control unit 14 may include any wired or wireless networking hardware, such as a modem, LAN port, wireless fidelity (Wi-Fi) card, WiMax card, mobile communications hardware, and/or other hardware for communicating with other networks and/or devices. Therefore, the communication between the control unit 14, the wheelchair 12, and/or other external devices may be provided through the network interface 706 via the wired or wireless communications, such as a network 714.

The network 714 may include a wide area network (WAN), such as the Internet, a local area network (LAN), a mobile communications network, a public service telephone network (PSTN), a personal area network (PAN), a metropolitan area network (MAN), a virtual private network (VPN), and/or another network that can electronically connected the control unit 14 to other components.

The data storage device 710, which may generally be a storage medium, may contain one or more data repositories for storing data that is received and/or generated, and may be any physical storage medium, including, but not limited to, a hard disk drive (HDD), memory, removable storage, and/or the like. While the data storage device 710 is depicted as a local device, it should be understood that the data storage device 710 may be a remote storage device, such as, for example, a server computing device or the like. Illustrative data that may be contained within the data storage device 710 is described below with respect to FIG. 7C and includes, but is not limited to, first actuator data 722, second actuator data 724, first position sensor data 726, second position sensor data 727, upper leg sensor data 730, lower leg sensor data 732 and catch data 734.

Referring again to FIGS. 1 and 7A, the wheelchair 12 may include a plurality of sensors that provide sensor data to effectuate the functionalities described herein. The plurality of sensors include, but are not limited to, the first position sensor 42, the second position sensor 44, an upper leg sensor 43, a lower leg sensor 45 and a mating sensor 51. It should be understood that more or fewer sensors may be provided.

Some embodiments include the first position sensor 42 operable to produce the first position sensor data 726 that is indicative of the position of the at least one brace assembly 38. That is, the first position sensor 42 may determine whether the at least one brace assembly 38 is in the retracted position, the deployed position, or a position therebetween. Further, in some embodiments, the first position sensor 42 may be a pressure sensor that determines that when the at least one brace assembly 38 are in the deployed position, the pair of flexible braces 60a, 60b (FIG. 4) are securely tight against the upper leg portion 18 of the user 16. That is, when the at least one brace assembly 38 is in the deployed position, due the variances in the size of the legs of the plurality of users, the first position sensor 42 detects whether the pair of flexible braces 60a, 60b (FIG. 4) will provide the required support by a relationship of a space or a gap between the upper leg portion 18 of the user 16 and the interior surface 62b (FIG. 4) of the pair of flexible braces 60a, 60b (FIG. 4). As a non-limiting example, the data storage device 710 may store example desirable and/or undesirable space and/or gap relationships. As a non-limiting example, the first position sensor 42 may be positioned within the at least one brace assembly 38 and have a field of view of the at least one brace assembly 38 as well as the pair of flexible braces 60a, 60b (FIG. 4).

Some embodiments include the second position sensor 44 operable to produce the second position sensor data 728 that is indicative of the position of the second brace assembly 40. That is, the second position sensor 44 may determine whether the second brace assembly 40 is in the retracted position, the deployed position, or a position therebetween. Further, in some embodiments, the second position sensor 44 may be a pressure sensor that determines that when the second brace assembly 40 is in the deployed position, the pair of flexible braces 60a, 60b (FIG. 4) are securely tight against the lower leg portion 19 of the user 16. That is, when the second brace assembly 40 is in the deployed position, due the variances in the size of the legs of the plurality of users, the second position sensor 44 detects whether the pair of flexible braces 60a, 60b (FIG. 4) will provide the required support by a relationship of a space or a gap between the lower leg portion 19 of the user 16 and the interior surface 62b (FIG. 4) of the pair of flexible braces 60a, 60b (FIG. 4). As a non-limiting example, the data storage device 710 may store example desirable and/or undesirable space and/or gap relationships. As a non-limiting example, the second position sensor 44 may be positioned within the second brace assembly 40 and have a field of view of the second brace assembly 40 as well as the pair of flexible braces 60a, 60b (FIG. 4).

Some embodiments further include an upper leg sensor 43 that provides data to determine the size and position of the upper leg portion 18 of the user 16. It should be appreciated that example upper leg sensor 43 may be an image device that transmits at least one image such that a position and/or size of the upper leg portion 18 of the user 16 may be determined. The position of the upper leg portion 18 of the user 16 is useful to understand such that the brace system 37 may be adjusted either mechanically, electrically, and/or pneumatically to match the exact location of the upper leg portion 18 of the user 16. In other examples, the example upper leg sensor 43 may be a laser, a position sensor, a force sensor, a transducer, any type of detector that is configured to perform the functionality described herein, and the like.

The wheelchair 12 may further include a lower leg sensor 45 that provides data to determine the size and position of the lower leg portion 19 of the user 16. It should be appreciated that example lower leg sensor 45 may be an image device that transmits at least one image such that a position and/or size of the lower leg portion 19 of the user 16 may be determined. The position of the lower leg portion 19 of the user 16 is useful to understand such that the brace system 37 may be adjusted either mechanically, electrically, and/or pneumatically to match the exact location of the lower leg portion 19 of the user 16. In other examples, the example lower leg sensor 45 may be a laser, a position sensor, a force sensor, a transducer, any type of detector that is configured to perform the functionality described herein, and the like.

The wheelchair 12 may also include a mating sensor 51 that is operable to determine whether each of the pair of the flexible braces 60a, 60b are connected, mated, and/or joined in the deployed position. The mating sensor 51 may be configured to detect whether the distal end 56 of the flexible brace 60a is received within the generally hook shape of the distal end 58 of the flexible brace 60b and/or whether the engagement portion 67 of flexible brace 60b is received in the attachment portion 66 of the distal end 56. It should be understood that it is useful to know whether each of the pair of the flexible braces 60a, 60b are connected, mated, and/or joined in the deployed position because when connected, joined and/or mated, the brace assembly 38 may provide additional rigidity and/or support to assist the user to transition between the plurality of user positions (e.g., transitioning from a sitting position to a standing position).

Figure 7C:
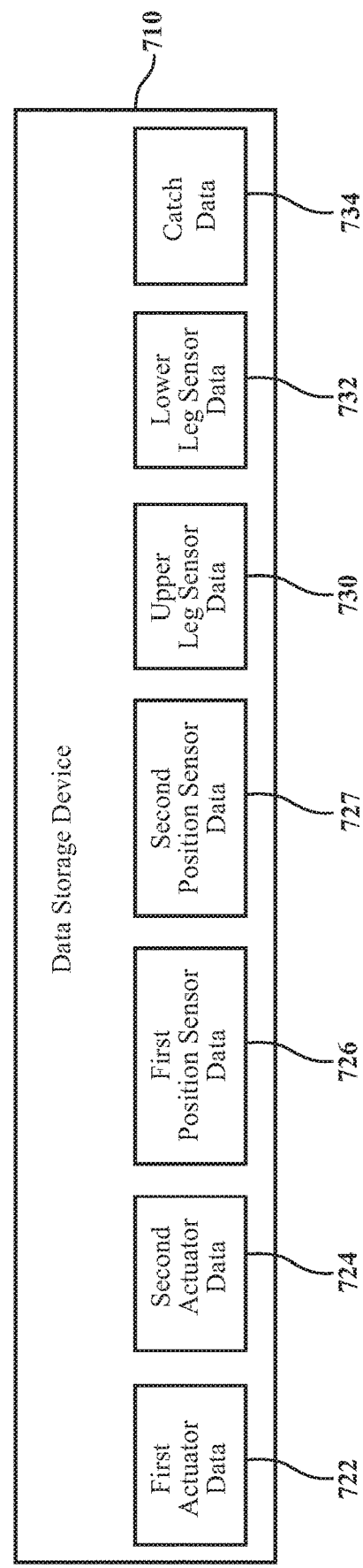
FIG. 7C schematically depicts example data stored within an example data storage device of the example wheelchair system of FIG. 7A according to one or more embodiments described and illustrated herein.

Referring now to FIG. 7C, the data storage device 710 may store data to perform the functionalities described herein, moving the brace system between the retracted and deployed positions to provide support to assist the user to transition between a plurality of user positions. Embodiments may include some, all, or more than the data depicted in FIG. 7C.

First actuator data 722 may be data related to the amount of fluid force (e.g., pound per square inch) currently within the at least one bladder 54, a minimum and/or maximum fluid level for the at least one bladder 54 (e.g., different sized flexible braces 60*a*, 60*b* will have different maximum and minimum, the type of fluid (e.g., liquid, gas, and the like), the type of actuator, and the like. Historical first actuator data 722 may be stored in the data storage device, which may be used by the control unit 14 to learn what minimum and/or maximum fluid level is appropriate for each particular sized pair of flexible braces 60*a*, 60*b*, for example.

Second actuator data 724 may be data related to the amount of fluid force (e.g., pound per square inch) currently within the at least one bladder 54, a minimum and/or maximum fluid level for the at least one bladder 54 (e.g., different sized flexible braces 60*a*, 60*b* will have different maximum and minimum, the type of fluid (e.g., liquid, gas, and the like), the type of actuator, and the like. Historical second actuator data 724 may be stored in the data storage device, which may be used by the control unit 14 to learn what minimum and/or maximum fluid level is appropriate for each particular sized pair of flexible braces 60*a*, 60*b*, for example.

First position sensor data 726 produced by the first position sensor 42, if provided, may also be stored in the data storage device 710. As stated above and described in more detail below, the first position sensor data 726 may be used to determine a position of the at least one brace assembly 38 (e.g. whether in a deployed position and/or a retracted position), to determine a position of the upper leg portion 18 of the user 16, and the like.

Second position sensor data 728 produced by the second position sensor 44, if provided, may also be stored in the data storage device 710. As stated above and described in more detail below, the second position sensor data 728 may be used to determine a position of the second brace assembly 40 (e.g. whether in a deployed position and/or a retracted position), to determine a position of the lower leg portion 19 of the user 16, and the like.

Other data in the form of upper leg sensor data 730 (e.g. the location and/or size of the upper leg portion of the user) produced by the upper leg sensor 43, lower leg sensor data 732 (e.g. the location and/or size of the lower leg portion of the user) produced by the lower leg sensor 45 and catch data 734 (e.g. whether the flexible braces are connected, mated and/or joined) by the mating sensor 51, if such sensors are provided, may be stored in the data storage device 710. Such data may be used to move the brace system 37 between the retracted and deployed positions to assist the user to transition between a plurality of user positions, as described in more detail below with respect to FIG. 8.

Referring once again to FIG. 1, the user 16 of a wheelchair 12 may use the brace system 37 to assist the user in transitioning between user positions, such as standing without the need for help of a second person. For example, the user 16 wheelchair 12 may want to reach an object on a shelf or within a cabinet. As such, the user may deploy the brace system 37 to lock in the legs of the user to wheelchair and the user's feet to, for example, the footrest of the wheelchair, such that the user may stand to reach the object. In another example, the user may deploy the brace system 37 to lock in the legs of the user to wheelchair with the user's feet in contact with a surface, such as a floor, such that the user may stand to reach the object.

Referring now to FIG. 8, an example method of moving the brace assembly between the retracted and deployed positions to assist the user to transition between the plurality of user positions is illustrated by a flowchart 800. The user may wish to enable the brace system by using an input device (e.g., a switch 27, the controller 28, or any other input device) at block 805 to enter into the assisting program that provides additional support and/or strength to the legs of the user to assist the user in moving or transitioning between the plurality of user positions. It should be understood that the user may enable/disable the brace system at any time, and he or she does not need to orientate or position the wheelchair in any special arrangement or orientation.

In some embodiments, the wheelchair may automatically enable/disable the brace system without a user input. In such embodiments, the brace system may detect the user attempting to transition between the plurality of user positions determined by using a plurality of sensors (e.g., first position sensor 42, second position sensor 44, upper leg sensor 43 and/or lower leg sensor 45).

After receiving user input, a position of the legs of the user is determined at block 810. The position of the legs of the user may be determined by using a plurality of sensors (e.g., first position sensor 42, second position sensor 44, upper leg sensor 43 and/or lower leg sensor 45), as described above. The brace system determines whether the legs of the user are in a proper position at block 815. If the system determines that the legs of the user are not in a desired position, then the user readjusts, at block 820. It should be appreciated that the user may be notified to readjust via a sound, a visual indicator, and/or the like. It should be understood that blocks 810-820 may continuously repeat until the legs of the user are in a desirable position. Once the legs of the user are in the desired position as determined at block 815, the position of the brace system is determined at block 825.

If the brace system is determined to be in the deployed position, at block 830, the control unit activates the first and/or second actuator via a control signal to retract the brace system, at block 835, until the brace system is determined to be in the retracted position, at block 840. It should be understood that blocks 835-840 may continuously repeat until the brace system is in the retracted position. Once in the retracted position, the user may resume normal use of the wheelchair, at block 845 and the illustrative method 800 ends at block 850.

If the brace system is determined to not be in the deployed position (i.e., in the retracted position), at block 830, the control unit activates the first and/or second actuator via a control signal such that the brace system moves from the retracted position into the deployed position, at block 855, until the brace system is determined to be in the deployed position, at block 860. It should be understood that blocks 855-860 may continuously repeat until the brace system is in the deployed position. Once in the deployed position at block 865, the user may transition between the plurality of user positions, at block 870.

As described above, and illustrated in FIG. 2, one of the plurality of user positions is the standing position. In the deployed position, the brace system provides support to the legs of the user, independent from an additional person such as an aide, to assist the user to transition between the sitting position into the standing position. In some embodiments, the wheelchair may also be actuated to raise in the system vertical direction (i.e., in the +Z direction) and/or to provide functions as an exoskeleton to also assist the user. It should be understood that the brace system may support the legs of the user against portions of the wheel chair, such as the seat portion, the footrest portion and the like, to provide additional rigidity and support for the user to transition between the plurality of user positions. Once deployed, the illustrative method 800 ends at block 850.

It should now be understood that the systems and methods described herein provide a wheelchair capable of providing a brace system that moves between retracted and deployed positions to provide a physical support to the legs of the user to assist the user in transition between a plurality of user positions. Embodiments determine a user request for such assistance and then either deploys and/or retracts the brace system. Embodiments provide for assistance independent of additional people, such as aides, to assist the user in moving or transitioning between the plurality of user positions while also allowing or permitting the wheelchair to function normally when the brace system is in the retracted position.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A wheelchair system comprising:
   a wheelchair comprising:
      a frame;
      a brace system coupled to the frame, the brace system comprising:
         a pair of braces,
         one or more inflatable devices coupled to each one of the pair of braces, the one or more inflatable devices are configured to inflate to at least partially circumferentially wrap around a portion of a pair of legs of a user to secure the user to the wheelchair,
      wherein, the brace system is movable between a retracted position and a deployed position such that in the deployed position, the pair of braces stabilize the user of the wheelchair to assist the user to transition between a plurality of user positions and in the retracted position, the pair of braces are housed in a receiving cavity.

2. The wheelchair system of claim 1, wherein the plurality of user positions includes a seated position and a standing position.

3. The wheelchair system of claim 1, wherein in the deployed position, a distal end of each of the pair of braces are moved in a direction towards one another.

4. The wheelchair system of claim 3, further comprising:
   a processing device, and
   a non-transitory, processor-readable storage medium in communication with the processing device, wherein the non-transitory, processor-readable storage medium comprising one or more programming instructions that, when executed, cause the processing device to:
      determine when a user request is initiated, and
      actuate at least one actuator to move the pair of braces into the deployed position and maintaining the deployed position of the pair of braces.

5. The wheelchair system of claim 3, wherein the distal end of one of the pair of braces moves with a greater radius with respect to a leg of the user such that the distal end of one of the pair of braces overlaps with the other distal end of the pair of braces in the deployed position.

6. The wheelchair system of claim 5, wherein:
   the distal end of the one of the pair of braces that moves with the greater radius with respect to the leg of the user includes an engagement portion and is configured to releasably engage with an attachment portion of the distal end of the other one of the pair of braces in the deployed position.

7. The wheelchair system of claim 1, further comprising:
   a plurality of elongated linkages positioned between an exterior surface and an interior surface of the pair of braces, and
   wherein the one or more inflatable devices are at least one bladder provided on the exterior surface of the pair of braces.

8. The wheelchair system of claim 7, wherein when the pair of braces are in the in the deployed position, the plurality of elongated linkages extend to provide rigidity to support each leg of the user during the transition between the plurality of user positions.

9. The wheelchair system of claim 1, wherein the one or more inflatable devices are at least one bladder provided between an exterior surface and an interior surface of the pair of braces.

10. The wheelchair system of claim 9, wherein the exterior surface is a first surface and the interior surface is second surface where the first surface is more rigid than the second surface.

11. A powered wheelchair system comprising:
    a wheelchair comprising:
       a frame;
       a brace system coupled to the frame, the brace system comprising:
          a pair of braces,
          one or more inflatable devices coupled to each one of the pair of braces,
       a processing device, and
       a non-transitory, processor-readable storage medium in communication with the processing device, wherein the non-transitory, processor-readable storage medium comprising one or more programming instructions that, when executed, cause the processing device to:
          determine when a user request is initiated, and
          actuate at least one actuator to inflate the pair of braces to move the brace system between a retracted position and a deployed position such that in the deployed position, the pair of braces stabilize a user of the wheelchair to assist the user to transition between a plurality of user positions.

12. The powered wheelchair system of claim 11, wherein the one or more inflatable devices are configured to at least partially circumferentially wrap around a portion of a pair of legs of a user to secure the user to the wheelchair in the deployed position.

13. The powered wheelchair system of claim 11, wherein in the retracted position, each one of the pair of braces are housed in a receiving cavity.

14. The powered wheelchair system of claim 11, wherein:
    in the deployed position, a distal end of each of the pair of braces are inflated in a direction towards one another, and wherein the distal end of one of the pair of braces inflates with a greater radius with respect to a leg of the user such that the distal end of one of the pair of braces overlaps with the other distal end of the pair of braces in the deployed position.

15. The powered wheelchair system of claim 14, wherein:
the distal end of the one of the pair of braces that inflates with a greater radius with respect to the leg of the user and includes an engagement portion and is configured to releasably engage with an attachment portion of the distal end of the other one of the pair of braces in the deployed position.

16. The powered wheelchair system of claim 15, wherein the distal end of one of the pair of braces that moves with the greater radius with respect to the leg of the user is a hook shape that is configured to receive a portion of the distal end of the other one of the pair of braces in the deployed position.

17. The powered wheelchair system of claim 11, further comprising:
a plurality of elongated linkages positioned between an exterior surface and an interior surface of the pair of braces, and wherein the one or more inflatable devices are at least one bladder provided on the exterior surface of the pair of braces.

18. The powered wheelchair system of claim 17, wherein when the pair of braces are in the in the deployed position, the plurality of elongated linkages extend to provide rigidity to support the user during the transition between the plurality of user positions.

19. The powered wheelchair system of claim 11, wherein:
the one or more inflatable devices are at least one bladder provided between an exterior surface and an interior surface of the pair of braces, and wherein the exterior surface is a first surface and the interior surface is second surface where the first surface is more rigid than the second surface.

* * * * *

UNITED STATES PATENT AND TRADEMARK OFFICE
CERTIFICATE OF CORRECTION

PATENT NO. : 11,628,108 B2
APPLICATION NO. : 16/910583
DATED : April 18, 2023
INVENTOR(S) : Douglas A. Moore It is certified that error appears in the above-identified patent and that said Letters Patent is hereby corrected as shown below:

In the Specification

In Column 7, Line(s) 5, delete "understand" and insert --understood--, therefor.

In the Claims

In Column 16, Line(s) 18, Claim 8, delete "in the in the" and insert --in the--, therefor.

In Column 18, Line(s) 5, Claim 18, delete "in the in the" and insert --in the--, therefor.

Signed and Sealed this
Twenty-sixth Day of December, 2023

Katherine Kelly Vidal
*Director of the United States Patent and Trademark Office*